(12) United States Patent
Ohyama et al.

(10) Patent No.: US 7,351,429 B1
(45) Date of Patent: Apr. 1, 2008

(54) ORAL SOLID PREPARATION

(75) Inventors: Toshinori Ohyama, Nogi-machi (JP); Masahiko Ohishi, Oyama (JP); Yasuhiro Yamamoto, Koshigaya (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 567 days.

(21) Appl. No.: 10/111,422

(22) PCT Filed: Nov. 10, 2000

(86) PCT No.: PCT/JP00/07904

§ 371 (c)(1),
(2), (4) Date: May 7, 2002

(87) PCT Pub. No.: WO01/34147

PCT Pub. Date: May 17, 2001

(30) Foreign Application Priority Data

Nov. 11, 1999 (JP) ................................. 11-320585

(51) Int. Cl.
*A61K 9/20* (2006.01)
*A61K 9/28* (2006.01)
*A01N 43/50* (2006.01)

(52) U.S. Cl. ...................... 424/465; 424/464; 424/474; 514/396; 514/400; 514/960

(58) Field of Classification Search ................ 424/400, 424/451, 452, 457, 463, 464, 465, 468, 474, 424/480; 514/396, 400, 960
See application file for complete search history.

(56) References Cited

U.S. PATENT DOCUMENTS

| 5,084,278 A | | 1/1992 | Mehta et al. | |
|---|---|---|---|---|
| 5,932,607 A | * | 8/1999 | Miyachi et al. | 514/399 |
| 5,948,437 A | * | 9/1999 | Parikh et al. | 424/464 |

FOREIGN PATENT DOCUMENTS

| EP | 0314387 | * | 5/1989 |
|---|---|---|---|
| EP | 314387 | | 5/1989 |
| EP | 733621 | | 9/1996 |
| EP | 0733621 A | * | 9/1996 |
| EP | 901787 | | 3/1999 |
| EP | 0901787 | * | 3/1999 |
| JP | 58-206533 | | 12/1983 |
| JP | 11-255649 | | 9/1999 |

* cited by examiner

*Primary Examiner*—Sharmila G. Landau
(74) *Attorney, Agent, or Firm*—Oblon, Spivak, McClelland, Maier & Neustadt, P.C.

(57) ABSTRACT

The invention is to provide an oral solid pharmaceutical that is uniform in the content of KRP-197, having bladder-selective anticholinergic activity, being a therapeutic drug for pollakiuria and urinary incontinence, and being active with a very low dosage, that can be taken quantitatively, and that is easy in the handling. Since KRP-197 becomes unstable to light under the influence of additives, the invention is to select the additives to be used and to obtain a pharmaceutical with high stability.

By formulating KRP-197 with drug-making carriers, a pharmaceutical that is uniform in the content, capable of taking quantitatively and easy in the handling has been provided. Furthermore, by using polyvinyl pyrrolidone for binder and by making into tablet coated with a coating base containing titanium dioxide and ferric oxide, a pharmaceutical capable of taking quantitatively and excellent in the light stability has been provided.

10 Claims, No Drawings

ORAL SOLID PREPARATION

TECHNICAL FIELD

The present invention relates to an oral solid pharmaceutical with a small amount of powder of 4-(2-methyl-1-imidazolyl)-2,2-diphenylbutylamide (hereinafter abbreviated as KRP-197), having selective anticholinergic activity on bladder and being a therapeutic drug for pollakiuria and urinary incontinence, made into an oral tablet capable of taking easily.

BACKGROUND TECHNOLOGIES

KRP-197 is a novel derivative having selective anticholinergic activity (Japanese Unexamined Patent Publication No. Hei 7-15943) and is promising as a therapeutic drug for pollakiuria and urinary incontinence (Miyachi H. et al, Bioorg. Med. Chem., 1999, 7, 1151-1161). No oral solid pharmaceutical that is uniform in the content of a small amount of active ingredient, excellent in the stability and capable of taking quantitatively on clinical application of KRP-197 has been known.

The subject of the invention is to provide an oral solid pharmaceutical that is uniform in the content of active ingredient contained in a small amount and capable of taking quantitatively. Additionally, since KRP-197 becomes unstable to light under the influence of additives, the subject is to provide an oral solid pharmaceutical with excellent stability to light.

DISCLOSURE OF THE INVENTION

The inventors have prepared an oral solid pharmaceutical that contains a small amount of active ingredient uniformly and is capable of taking quantitatively on clinical application of KRP-197, leading to the completion of the invention. The inventive oral solid pharmaceutical is an oral solid pharmaceutical (tablet) with uniform content, prepared by formulating a small amount of KRP-197 with drug-making carriers (excipient, disintegrator, binder, lubricant and coating agent) and by granulating, pressing into tablet and coating.

According to the invention, by formulating a small amount of powder of KRP-197 with drug-making carriers and making into tablet, a pharmaceutical easy to take quantitatively can be provided. Moreover, by using polyvinyl pyrrolidone as a binder and further by coating with a coating solution containing titanium dioxide and ferric oxide, a pharmaceutical with uniform content and good light stability can be provided.

The process for preparing the inventive pharmaceutical comprises the steps of mixing the excipient (for example, saccharides such as lactose and glucose, sugar alcohols such as D-sorbitol and mannitol, celluloses such as microcrystalline cellulose, starches such as partially pregelatinized starch and corn starch, etc., preferably partially pregelatinized starch, lactose or microcrystalline cellulose) and the disintegrator (for example, celluloses such as calcium carboxymethylcellulose, low substituted hydroxypropylcellulose, sodium cross carmelose and methylcellulose, cross povidone, etc., preferably low substituted hydroxypropylcellulose), and further by adding the binder (for example, celluloses such as hydroxypropylcellulose, hydroxypropylmethylcellulose, ethylcellulose and methylcellulose, gelatin, polyvinyl alcohol, partially hydrolyzed polyvinyl alcohol, polyvinyl pyrrolidone, etc., preferably partially hydrolyzed polyvinyl alcohol or polyvinyl pyrrolidone), followed by granulation. The granulation can be performed by wet granulation process, fluidized bed granulation process or dry granulation process, but, at this time, the fluidized bed granulation process can be used well.

Following this, the lubricant (for example, magnesium stearate, calcium stearate, talc, hydrogenated oil, etc., preferably magnesium stearate) is added, the mixture is pressed into tablet, and further the coating agent (for example, celluloses such as hydroxypropylcellulose, hydroxypropylmethylcellulose, ethylcellulose and methyl-cellulose, hydroxypropylmethylcellulose phthalate, methacrylic acid copolymer, titanium dioxide, ferric oxide, carnauba wax, etc., preferably hydroxypropylmethylcellulose, titanium dioxide, ferric oxide or carnauba wax) is coated, thereby the oral solid pharmaceutical or tablet capable of taking more easily can be obtained.

Furthermore, the preparation of oral solid pharmaceutical with improved light stability can be accomplished by using polyvinyl pyrrolidone as a binder and further by coating with a coating solution containing titanium dioxide and ferric oxide. Upon granulation at this time, an aqueous solution containing KRP-197 and polyvinyl pyrrolidone is sprayed and granulation and drying are performed, followed by addition of lubricant, pressing into tablet, and coating. At this time, if coating with a coating solution containing titanium dioxide and ferric oxide, a tablet with improved stability to light as well as uniform content can be obtained.

In the tablet obtained in this way, 0.025 mg to 2 mg of KRP-197 can be contained uniformly as an active ingredient per tablet, and, by taking orally, the pharmaceutical can be taken quantitatively.

BEST EMBODIMENT TO PUT THE INVENTION INTO PRACTICE

In following, the invention will be illustrated based on the examples, but the invention is not confined to these examples.

Example 1

Per tablet, 0.05 mg of KRP-197 and 16 mg of partially pregelatinized starch were mixed, then 63.71 mg of microcrystalline cellulose were added thereto and mixed. Further, 0.24 mg of magnesium stearate were added and mixed, followed by pressing into tablet to obtain a plane tablet. Onto the plane tablet thus obtained, 4 mg-equivalent hydroxypropylmethylcellulose 2910 was coated, and then 0.002 mg of carnauba wax were added and mixed to obtain a film-coated tablet.

Example 2

Per tablet, 0.25 mg of KRP-197 and 23 mg of partially pregelatinized starch were mixed, then 92.45 mg of microcrystalline cellulose were added thereto and mixed. Further, 0.3 mg of magnesium stearate were added and mixed, followed by pressing into tablet to obtain a plane tablet. Onto the plane tablet thus obtained, 4 mg-equivalent hydroxypropylmethylcellulose 2910 was coated, and then 0.002 mg of carnauba wax were added and mixed to obtain a film-coated tablet.

Example 3

Per tablet, 2 mg of KRP-197 and 24.6 mg of partially pregelatinized starch were mixed, then 108 mg of microcrystalline cellulose were added thereto and mixed. Further, 0.4 mg of magnesium stearate were added and mixed, followed by pressing into tablet to obtain a plane tablet. Onto the plane tablet thus obtained, 5 mg-equivalent hydroxypropylmethylcellulose 2910 was coated, and then 0.002 mg of carnauba wax were added and mixed to obtain a film-coated tablet.

Example 4

Per tablet, 2 mg of KRP-197, 86.85 mg of lactose, 29 mg of microcrystalline cellulose and 13.5 mg of low substituted hydroxypropylcellulose were mixed, then an aqueous solution of 2.7 mg-equivalent partially hydrolyzed polyvinyl alcohol was added, and the mixture was milled, granulated and dried. Thereto, 5 mg of magnesium stearate were added and mixed, followed by pressing into tablet to obtain a plane tablet. Onto the plane tablet thus obtained, 5 mg-equivalent hydroxypropylmethylcellulose 2910 was coated, and then 0.002 mg of carnauba wax were added and mixed to obtain a film-coated tablet.

Example 5

Per tablet, 0.025 mg of KRP-197, 15.945 mg of partially pregelatinized starch were mixed, then 63.79 mg of microcrystalline cellulose were added thereto and mixed. Further, 0.24 mg of magnesium stearate were added and mixed, followed by pressing into tablet to obtain a plane tablet. Onto the plane tablet thus obtained, 4 mg-equivalent hydroxypropylmethylcellulose 2910 was coated, and then 0.002 mg of carnauba wax were added and mixed to obtain a film-coated tablet.

Example 6

Per tablet, 18.7 mg of partially pregelatinized starch and 74.975 mg of microcrystalline cellulose were taken. Then, using a fluidized bed granulation device, an ethanol-water solution of 0.025 mg of KRP-197 and 1 mg-equivalent polyvinyl pyrrolidone was sprayed thereto, and the mixture was granulated and dried. After screening and rectifying the granules, 0.3 mg of magnesium stearate were added and mixed, followed by pressing into tablet to obtain a plane tablet. Onto the plane tablet thus obtained, a suspension of 4.5 mg-equivalent hydroxypropylmethylcellulose 2910, 0.43 mg-equivalent titanium dioxide and 0.07 mg-equivalent ferric oxide was coated, and then 0.002 mg of carnauba wax were added and mixed to obtain a film-coated tablet.

Example 7

Per tablet, 26.4 mg of partially pregelatinized starch and 105.75 mg of microcrystalline cellulose were taken. Then, using a fluidized bed granulation device, an ethanol-water solution 0.05 mg of KRP-197 and 1.4 mg-equivalent polyvinyl pyrrolidone was sprayed thereto, and the mixture was granulated and dried. After screening and rectifying the granules, 0.4 mg of magnesium stearate were added and mixed, followed by pressing into tablet to obtain a plane tablet. Onto the plane tablet thus obtained, a suspension of 5.4 mg-equivalent hydroxypropylmethylcellulose 2910, 0.52 mg-equivalent titanium dioxide and 0.08 mg-equivalent ferric oxide was coated, and then 0.002 mg of carnauba wax were added and mixed to obtain a film-coated tablet.

Example 8

Per tablet, 26.4 mg of partially pregelatinized starch and 105.7 mg of microcrystalline cellulose were taken. Then, using a fluidized bed granulation device, an ethanol-water solution of 0.1 mg of KRP-197 and 1.4 mg-equivalent polyvinyl pyrrolidone was sprayed thereto, and the mixture was granulated and dried. After screening and rectifying the granules, 0.4 mg of magnesium stearate were added and mixed, followed by pressing into tablet to obtain a plane tablet. Onto the plane tablet thus obtained, a suspension of 5.4 mg-equivalent hydroxypropyl-methylcellulose 2910, 0.52 mg-equivalent titanium dioxide and 0.08 mg-equivalent ferric oxide was coated, and then 0.002 mg of carnauba wax were added and mixed to obtain a film-coated tablet.

Example 9

Per tablet, 30.4 mg of partially pregelatinized starch and 121.35 mg of microcrystalline cellulose were taken. Then, using a fluidized bed granulation device, an ethanol-water solution of 0.25 mg of KRP-197 and 1.6 mg-equivalent polyvinyl pyrrolidone was sprayed thereto, and the mixture was granulated and dried. After screening and rectifying the granules, 0.4 mg of magnesium stearate were added and mixed, followed by pressing into tablet to obtain a plane tablet. Onto the plane tablets thus obtained, a suspension of 5.4 mg-equivalent hydroxypropyl-methylcellulose 2910, 0.52 mg-equivalent titanium dioxide and 0.08 mg-equivalent ferric oxide was coated, and then 0.002 mg of carnauba wax were added and mixed to obtain a film-coated tablet.

Experimental Example 1

With the tablets containing 0.025 mg of KRP-197 obtained in Example 5 and Example 6, which are most liable to be influenced by additives in the stability, decomposition products under light irradiation of up to 1.2 million Lux·hr in the non-packaged state were determined by high-speed liquid chromatograph method. As a result, the tablet obtained in Example 6 showed good stability, hence the effect of additions of polyvinyl pyrrolidone, titanium dioxide and ferric oxide was ascertained. The measurement results of decomposition products are shown in Table 1.

TABLE 1

| | Evaluation results of stability of 0.025 mg KRP-197 tablet (content of main decomposition products, %) | |
|---|---|---|
| | Example 5 | Example 6 |
| Start | No detection | No detection |
| 1.2 million Lux · hr | 13.6% | <0.16% |

Experimental Example 2

With the tablets obtained in respective examples from Example 1 through Example 9, results obtained according to the uniformity test of content in the 13th revision Japanese Pharmacopoeia are shown in Table 2.

TABLE 2

Test results of uniformity of content of KRP-197 tablet

|  | Example 1 | Example 2 | Example 3 | Example 4 | Example 5 | Example 6 | Example 7 | Example 8 | Example 9 |
|---|---|---|---|---|---|---|---|---|---|
| Av. value (5) | 96.1 | 96.2 | 100.6 | 98.8 | 99.0 | 99.5 | 100.4 | 100.3 | 101.1 |
| Range (%) | 93.0-98.2 | 94.6-97.6 | 97.5-100.1 | 97.5-100.1 | 97.0-100.6 | 97.2-102.7 | 99.0-101.3 | 99.7-101.4 | 99.7-102.4 |
| Judgment value (%) | 7.9 | 6.0 | 3.7 | 3.2 | 4.1 | 2.6 | 1.9 | 1.5 | 2.8 |

Judgment value: Value less than 15% conform to the standard.

UTILIZABILITY IN THE INDUSTRY

According to the invention, by formulating KPP-197, having bladder-selective anticholinergic actibity and being a therapeutic drug for pollakiuria and urinary incontinence, with drug-making carriers and by converting to tablet, it has become possible to make the active ingredient that was difficult to take quantitatively, if keeping it powdery as it is, because of extremely small amount, into an oral solid pharmaceutical that is uniform in the content of ingredient and also easy in the handling, thus allowing to take quantitatively. In addition, by using polyvinyl pyrrolidone for binder and using titanium dioxide and ferric oxide for coating base, it has become possible to provide a pharmaceutical with improved stability to light.

The invention claimed is:

1. An oral solid pharmaceutical in tablet form comprising 0.025 to 2 mg of 4-(2-methyl-1-imidazolyl)-2,2-diphenyl-butylamide as an active ingredient, excipient, binder, lubricant and coating agent, which is obtained by spraying a solution of the active ingredient and the binder on the excipient, granulating and then drying the resultant mixture, pressing the granulated and dried mixture to give a plane tablet in the presence of the lubricant, and then coating the plane tablet with the coating agent to give a coated tablet, wherein the coating agent comprises titanium dioxide and ferric oxide in an mg-equivalent ratio of between 43:7 and 52:8.

2. The oral solid pharmaceutical of claim 1, which additionally contains a disintegrator.

3. The oral solid pharmaceutical of claim 2, wherein the excipient comprises at least one of partially pregelatinized starch, lactose and microcrystalline cellulose, the disintegrator comprises low substituted hydroxypropylcellulose, the binder comprises at least one of partially hydrolyzed polyvinyl alcohol and polyvinyl pyrrolidone, the lubricant comprises magnesium stearate, and the coating agent additionally comprises at least one of hydroxypropylmethylcellulose, and carnauba wax.

4. The oral solid pharmaceutical of claim 2, wherein the binder comprises polyvinyl pyrrolidone.

5. The oral solid pharmaceutical of claim 2, wherein the solution is an aqueous ethanol solution.

6. The oral solid pharmaceutical of claim 4, wherein the solution is an aqueous ethanol solution.

7. The oral solid pharmaceutical of claim 1, wherein the excipient comprises at least one of partially pregelatinized starch, lactose and microcrystalline cellulose, the binder comprises at least one of partially hydrolyzed polyvinyl alcohol and polyvinyl pyrrolidone, the lubricant comprises magnesium stearate, and the coating agent additionally comprises at least one of hydroxypropylmethylcellulose, and carnauba wax.

8. The oral solid pharmaceutical of claim 1, wherein the binder comprises polyvinyl pyrrolidone.

9. The oral solid pharmaceutical of claim 1, wherein the solution is an aqueous ethanol solution.

10. The oral solid pharmaceutical of claim 8, wherein the solution is an aqueous ethanol solution.

* * * * *